United States Patent
Gilligan

(10) Patent No.: US 8,597,573 B2
(45) Date of Patent: Dec. 3, 2013

(54) CONTINUOUSLY REGULATED PRECISION PRESSURE FLUID DELIVERY SYSTEM

(75) Inventor: Thomas Boyd Gilligan, Navasota, TX (US)

(73) Assignee: XY, LLC, Navasota, TX (US)

( * ) Notice: Subject to any disclaimer, the term of this patent is extended or adjusted under 35 U.S.C. 154(b) by 0 days.

(21) Appl. No.: 13/376,144

(22) PCT Filed: Jun. 3, 2010

(86) PCT No.: PCT/US2010/001630
§ 371 (c)(1),
(2), (4) Date: Dec. 2, 2011

(87) PCT Pub. No.: WO2010/141096
PCT Pub. Date: Dec. 9, 2010

(65) Prior Publication Data
US 2012/0085422 A1   Apr. 12, 2012

Related U.S. Application Data

(60) Provisional application No. 61/217,927, filed on Jun. 5, 2009.

(51) Int. Cl.
*G01N 15/06* (2006.01)

(52) U.S. Cl.
USPC ................ 422/81; 422/50; 422/68.1; 436/43; 436/180

(58) Field of Classification Search
USPC ................................ 422/50, 68.1, 81; 436/43
See application file for complete search history.

(56) References Cited

U.S. PATENT DOCUMENTS

| | | | |
|---|---|---|---|
| 3,758,175 A * | 9/1973 | Van Roojen | 384/12 |
| 4,503,385 A | 3/1985 | Haynes | |
| 6,280,408 B1 * | 8/2001 | Sipin | 604/65 |
| 6,662,818 B2 | 12/2003 | Paul et al. | |
| 7,887,520 B2 * | 2/2011 | Simon | 604/248 |
| 8,418,654 B2 * | 4/2013 | Hurwitz | 119/603 |
| 2003/0145886 A1 | 8/2003 | Paul et al. | |

FOREIGN PATENT DOCUMENTS

| | | |
|---|---|---|
| EP | 0 131 287 A1 | 1/1985 |
| EP | 0 317 809 A2 | 5/1989 |
| EP | 0317809 A2 | 5/1989 |
| EP | 0602416 A1 | 6/1994 |
| GB | 2428281 A | 1/2007 |
| WO | 2006-115663 A2 | 11/2006 |
| WO | 2008-096101 A2 | 8/2008 |

OTHER PUBLICATIONS

New Zealand Examination Report dated Oct. 8, 2012 issued in corresponding NZ Application No. 596847 (2 pages).
PCT International Search Report and Written Opinion dated Oct. 7, 2010 issued in corresponding PCT Application No. PCT/US2010/001630 (15 pages).

(Continued)

*Primary Examiner* — Brian J Sines
(74) *Attorney, Agent, or Firm* — Ryan Christensen; Cindee R. Ewell

(57) ABSTRACT

A fluid flow characteristic regulator (58) which provides a variable volume flow path in which a fluid flow can be continuously adjusted by a control fluid (57) to regulate at least one fluid flow characteristic of the fluid flow (11) within the variable volume flow path.

18 Claims, 11 Drawing Sheets

(56) References Cited

OTHER PUBLICATIONS

Colombian Office Action dated May 16, 2013 in corresponding CO Patent Application No. 11-181874 (2 pg. English Summary included). 8 pages.
New Zealand Notice of Acceptance dated Jul. 10, 2013 in corresponding NZ Patent Application No. 596847.
Japanese Office Action dated Jul. 8, 2013 in corresponding JP Patent Application No. 2012-513939.
Mexico Office Action dated Jul. 19, 2013 in corresponding MX Patent Application No. a/2011/012868.
Japanese Laid-Open Publication No. 62-279415 (English Abstract Attached) 6 pages.
Japanese National Phase PCT Laid-Open Publication No. 2008-529155 (Machine Translated Technical Field and Claims Attached) 17 pages.
Japanese National Phase PCT Laid-Open Publication No. 2003-167632 (English Abstract and Machine Translated Claims) 6 pages.
Japanese National Phase PCT Laid-Open Publication No. 2004-291187 (English Abstract and Machine Translated Claims) 12 pages.
Japanese National Phase PCT Laid-Open Publication No. 2003-142612 (English Abstract and Machine Translated Claims) 11 pages.
Japanese Utility Model Laid-Open Publication No. 06-011007 (Machine Translated Technical Field and Claims) 7 pages.
Japanese National Phase PCT Laid-Open Publication No. 2005-517232 (Machine Translated Technical Field and Claims) 22 pages.
Japanese Laid-Open Publication No. 01-287442 (English Abstract) 13 pages.
Japanese Laid-Open Publication No. 59-059238 (English Abstract) 6 pages.
Korean Office Action dated May 8, 2013 issued in corresponding KR Application No. 10-2011-7030007 (6 pages).
New Zealand Further Examination Report dated Jun. 11, 2013 in corresponding NZ Application No. 596847 (1 page).
PCT International Preliminary Report on Patentability dated Sep. 27, 2011 in PCT Application No. PCT/US10/01630. (5 pages).
AU Patent Examination Report No. 1 dated Sep. 6, 2013, issued in corresponding AU Appl No. 2010257174 (3 pages).

* cited by examiner

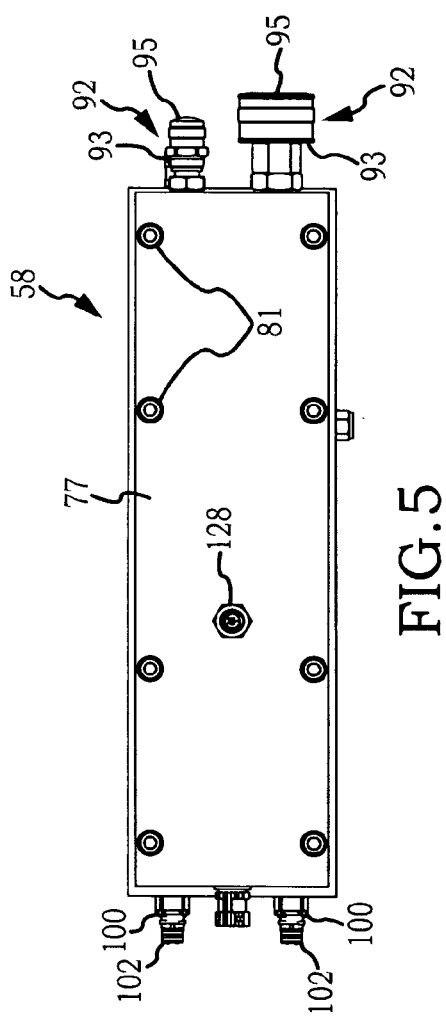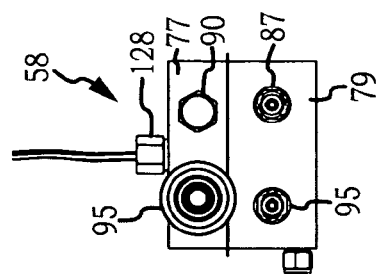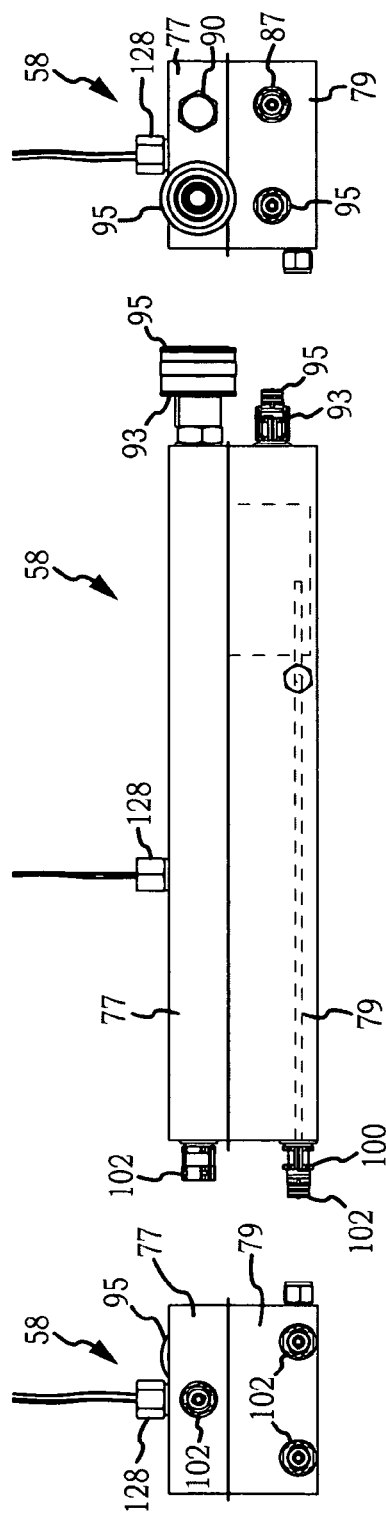

CONTINUOUSLY REGULATED PRECISION PRESSURE FLUID DELIVERY SYSTEM

This application is the U.S. National Stage of International Patent Cooperation Treaty Patent Application PCT/US2010/001630 which claims the benefit of U.S. Provisional Patent Application No. 61/217,927, filed Jun. 5, 2009, each hereby incorporated by reference.

I. TECHNICAL FIELD

A fluid flow characteristic regulator which provides a variable volume flow path in which a fluid flow can be continuously adjusted by a control fluid to regulate at least one fluid flow characteristic of the fluid flow within the variable volume flow path.

II. BACKGROUND

Precisely formulated, and in some cases sterile filtered fluids, are conventionally delivered to microfluidic devices such as liquid chromatographs and Fluorescent Activated Cell Sorters (FACS) during operation.

Conventional delivery of fluids to microfluidic devices may be limited by the amount of fluid contained by the fluid source connected to the microfluidic instrument. For example, the fluid source typically utilized to deliver sheath fluid to a FACS provides a 20 liter sheath fluid tank into which sheath fluid is transferred. The headspace in the fluid source can be subsequently pressurized to deliver sheath fluid from the fluid source to the FACS. An alternate form of fluid source for a FACS can include a flexible vessel which holds about 20 liters of sheath fluid. The flexible vessel holding the sheath fluid can be inserted into the sheath fluid tank. The headspace between the sheath fluid tank and the flexible vessel can be sufficiently pressurized to decrease the volume of the flexible vessel to forcibly urge the sheath fluid from the flexible vessel to the FACS. As to either example, the period of continuous operation of the FACS is limited to the amount of sheath fluid contained in the sheath fluid tank or flexible vessel. However, the construction of sheath fluid tanks which can contain more than 20 liters of sheath fluid and the provision of load-lifting equipment to transfer flexible sheath fluid vessels containing more than 20 liters of sheath fluid can be prohibitively expensive. Additionally, with larger pressurized containers, cleaning and fluid changing procedures typically take longer, as the air headspace of such pressurized containers are larger and may take longer to de-pressurize and re-pressurize to operating pressure.

Conventional delivery of fluids to microfluidic devices by pressurization of the headspace of the fluid source may also form or entrap small bubbles in the contained fluids. These small bubbles caused by pressure changes in the fluid can intermittently interfere with the operation of a FACS or liquid chromatograph by adherence to locations in the fluid stream resulting in undesired turbulent flow proximate the point of analysis.

Conventional delivery of sterile fluids to microfluidic devices can be expensive due to the cost of the sterile packaging materials in which fluids are contained. As a non-limiting example, sterile packaging materials are a major fraction of the overall cost of manufacturing ready-to-use sheath fluids for FACS. The fraction of packing costs can be significantly reduced in larger formats such as 100 liter drums as compared to 20 liter flexible vessels.

Conventional delivery of fluids to microfluidic devices utilize the fluid source as both a reservoir for fluid and as a regulator of fluid flow or fluid flow characteristics. As one non-limiting example, pressurized sheath fluid tanks utilized with FACS function both as a reservoir for an amount of sheath fluid and as a regulator with respect to the sheath fluid pressure and sheath fluid flow rate. If a greater or lesser sheath fluid pressure or sheath fluid flow rate is desired, the pressure in the headspace of the sheath fluid tank may be correspondingly increased or decreased to achieve the desired value. However, use of the fluid source to perform a plurality of functions can impose a limit on constructional form of the fluid source.

Conventional delivery of fluids to a microfluidic device can have fluid flow characteristics which change between the fluid source and the microfluidic device. As a non-limiting example, in the operation of a FACS using a pressurized sheath fluid tank, the operating pressure of the sheath fluid can be regulated by adjusting pressure of the gas in the headspace of the sheath fluid tank. However, the sheath fluid pressure at the nozzle of the FACS can be different than the sheath fluid pressure delivered from the sheath fluid tank requiring compensation through further adjustment of the gas pressure in the headspace of the sheath fluid tank. The causes of the change in sheath fluid pressure change may be related to effects of hydrostatic pressure based on the difference in height between the sheath fluid tank (corresponding to the height of the sheath fluid) and the nozzle of the FACS or resistive forces in the fluid flow path between the sheath fluid tank and the nozzle of the FACS, or combination of both. One source of resistive force in the fluid flow path can be a filter through which pressurized sheath fluid passes. The conventional manner of addressing this problem is to use a relatively large high volume filter, even though a FACS such as a MOFLO SX® having a 70μ diameter nozzle orifice, consumes only about 350-380 milliliters (mL) of sheath fluid per hour. While use of such a filter reduces change in pressure across the filter, there is a corresponding disadvantage in the dead volume space of the filter which makes clean-in-place procedures lengthy (more than 15 minutes and in most cases nearly 60 minutes).

Conventional delivery of fluids to microfluidic devices can have variation in one or more fluid flow characteristics in excess of the useful operating parameters of a particular microfluidic device or the method of analysis. Excess variation in fluid flow characteristics may be related to the fluid flow temperature, fluid flow pressure, fluid flow rate, amplitude or frequency of a fluid pressure waveform, amplitude or frequency of a fluid temperature waveform, amplitude or frequency of a fluid flow rate waveform. With respect to certain FACS and liquid chromotographs, variation in fluid flow characteristics has been conventionally addressed as above-described with the corresponding disadvantages.

The instant invention addresses each of these disadvantages in the conventional delivery of fluids to microfluidic devices for the purpose of regulating variation in fluid flow characteristics or increasing processing and analytical efficiency.

III. DISCLOSURE OF INVENTION

Accordingly, a broad object of the invention can be to provide a fluid flow characteristic regulator which can be utilized with any of a variety of microfluidic devices to isolate the function of providing an amount of fluid within a fluid source from the function of providing regulation of fluid flow characteristics of a fluid flow delivered to a microfluidic device.

Another broad object of the invention can be to provide a fluid flow characteristic regulator which operates to reduce the amount of variation in one or more fluid flow characteristics of a fluid flow such as fluid flow rate, fluid flow temperature, fluid flow pressure, amplitude or frequency of a fluid pressure waveform, amplitude or frequency of a fluid temperature waveform, amplitude or frequency of a fluid flow rate waveform.

Another broad object of the invention can be to provide a fluid flow characteristic regulator which functions in part to sterile filter the fluid flow with a reduced dead volume of about one fifth to about one twenty fifth of the conventional dead volume.

Another broad object of the invention can be to replace conventional pressurized fluid sources for FACS with an unpressurized fluid source fluidicly coupled to a reciprocating piston pump with the fluid flow delivered to a fluid flow characteristic regulator which sufficiently reduces variation in the fluid flow delivered from the pump to allow sorting of particles such as cells or sperm cells based on difference in one or more a cell characteristics such as the amount of DNA between X chromosome bearing sperm cells and Y chromosome bearing sperm cells.

Naturally, further objects of the invention are disclosed throughout other areas of the specification, drawings, and claims.

IV. BRIEF DESCRIPTION OF THE DRAWINGS

FIG. 1 provides a block diagram of a generic embodiment of the invention.

FIG. 2 provides a block diagram of hardware means and software means which may be utilized to practice various embodiments of the invention.

FIG. 5 is a plan view of a particular embodiment of a fluid flow characteristic regulator.

FIG. 6 is a side view of a particular embodiment of a fluid flow characteristic regulator.

FIG. 7 is a first end view of a particular embodiment of a fluid flow characteristic regulator.

FIG. 8 is a second end view of a particular embodiment of a fluid flow characteristic regulator.

V. MODE(S) FOR CARRYING OUT THE INVENTION

Generally, a fluid processing system which includes both devices and methods for the delivery of fluids with reduced variation in one or more fluid flow characteristics. Specifically, a fluid flow characteristic regulator which provides a variable volume flow path in which a fluid flow can be continuously adjusted by a control fluid to regulate at least one fluid flow characteristic of the fluid flow within the variable volume flow path.

DEFINITIONS

For the following defined terms, these definitions shall be applied, unless a different definition is given in the claims or elsewhere in this specification.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result.

For the purposes of the present invention, the term "a", "an", and "the" entity includes the plural referents unless the content clearly dictates otherwise. Thus as a non-limiting example, "a fluid" refers to one or more of those fluids. As such, the terms "a" or "an", "one or more" and "at least one" can be used interchangeably herein.

Figure 1:
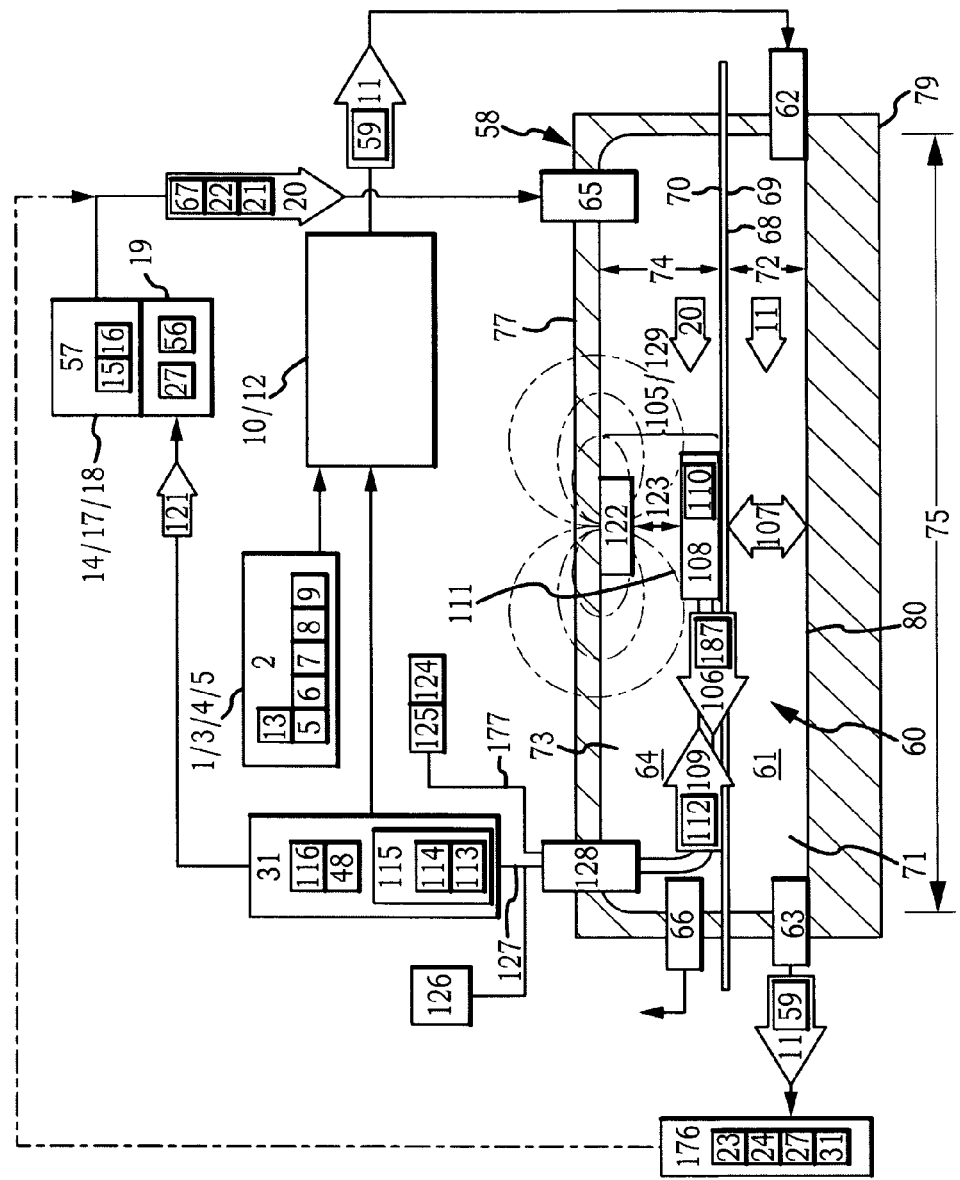

Now referring primarily to FIG. 1, embodiments of the invention can include a fluid source (1). In general, the fluid source (1) can be of any configuration capable of containing an amount of fluid (2). In certain applications, such as high pressure liquid chromatography the fluid source (1) can for example comprise a container (3) such as a bottle made of plastic or glass. In other applications, such as flow cytometry the fluid source (1) can for example be a sheath fluid tank (4), a flexible bag (5) containing an amount of fluid (2), or a flexible bag (5) which inserts into the sheath fluid tank (4).

Depending on the application, the amount of fluid (2) contained within the fluid source (1) can be an amount of gas (6) or an amount of liquid (7). The amount of gas (6) can be one kind of gas such as argon, nitrogen, carbon dioxide, helium, oxygen, various kinds of hydrocarbons, or the like, or can be a mixture of two or more gases having similar or dissimilar partial pressures, atmospheric gases, or a gas which carries an amount of vapor such as water vapor, or the like. An amount of liquid (7) can be a liquefied gas such as liquefied petroleum gas, liquefied carbon dioxide, supercritical carbon dioxide, or a solvent such as water, an alcohol, an acid, a base, an organic solvent such as an ether, acetonitrile, acetone, ethyl acetate, benzene, carbon tetrachloride, diethyl ether, or the like, or a solvent containing an amount of solute such as a salt, a pH buffering salt, a sugar, a starch, a soluble polymer, an organic acid, a surfactant, an amino acid, a protein, a nucleotide, a nucleoside, a chelating agent, an antioxidant, carbon dioxide, oxygen, or the like, or a liquid containing particles such as inorganic particles, organic particles, or biological particles such a nucleic acids, peptides, proteins, cells, or sperm cells. As to certain embodiments of the invention the amount of fluid (2) can be a sheath fluid (8) for use in flow cytometry including without limitation aqueous solutions of tris(hydroxymethyl)aminomethane ("TRIS") (also known as TRIZMA®) base, (4-(2-hydroxyethyl)-1-piperazineethanesulfonic acid) ("HEPES") citric acid, fructose, physiological saline buffer which can contain sodium phosphate, potassium phosphate, sodium chloride, or the like, or as to other embodiments can be a mobile phase (9) for use in chromatography or microfluidic particle analysis. However, these examples are not intended to be limiting with regard to the numerous and wide variety of fluids (2) (whether an amount of gas or an amount of liquid) which can be contained by the fluid source (1) and utilized with embodiments of the invention.

Again referring primarily to FIG. 1, embodiments of the invention can further include a fluid flow generator (10). The fluid flow generator (10) functions to generate a fluid flow (11) from the fluid source (1). The fluid flow generator (10) can for example be a liquid chromatography pump (12) such as a single piston, or a dual piston, proportioning valve, or other type of chromatography pump, or as to other applications, the fluid source (1) may be pressurized to generate the fluid flow (11) of the amount of fluid (2) from the fluid source (1) or an amount of pressure (13) which acts on a flexible bag (5) inserted within the fluid source (1).

Again referring primarily to FIG. 1, embodiments of the invention can further include a control fluid source (14). Typically, the control fluid source (14) can comprise any manner of container capable of containing a control fluid (57) such as an amount of compressed gas (15) or compressed liquid (16). As one non-limiting example, the control fluid source (14) can be a compressed gas cylinder (17) which can be obtained in numerous and varied configurations such as a K size (9.25 inches×60 inches) compressed gas cylinder (17) having an internal volume of about 49.9 liters. Alternately, the control fluid source (14) can be an air compressor (18) (or the tank of the air compressor) such as an Ingersoll Rand Horizontal Electric Air Compressor Model #3000E20FP. The forgoing examples are not intended to be limiting with respect to the configuration or operation of the control fluid source (14) to contain a control fluid (57) (which depending upon the embodiment can be an amount of compressed gas (15) or compressed liquid (16)). The amount of compressed gas (15) can be one kind of gas such as argon, nitrogen, carbon dioxide, helium, oxygen, or can be a mixture of two or more gases having similar or dissimilar partial pressures, atmospheric gases, or the like. However, these examples of compressed gas (15) contained within the control fluid source (14) is not intended to be limiting with respect to the numerous and varied gases or mixtures of gases which can be utilized with particular embodiments of the invention.

Again referring primarily to FIG. 1, the invention can further include a control fluid controller (19) coupled to the control fluid source (14). The control fluid controller (19) operates to control delivery of a control fluid flow (20) from the control fluid source (14) whether intermittent delivery or continuous delivery. The control fluid controller (14) depending upon the embodiment of the invention operates to adjust the pressure, volume, rate, temperature, or other control fluid characteristic (67) of the control fluid flow (20) (whether a control gas flow (21) or a control liquid flow (22) intermittently or continuously delivered from the control fluid source (14).

As to particular embodiments of the invention, the control fluid controller (19) can be a manual fluid controller (56) coupled to the control fluid controller (19) to control delivery of the control fluid (57) whether an amount of compressed gas (15) or an amount of compressed liquid (16)) from the control fluid source (14) as to volume, rate, pressure, temperature, or the like. As a non-limiting examples, manual fluid controllers (56) suitable for use with the invention include Seimens gas pressure regulator Model Number 41-100 or Parker Pneutronics gas pressure regulator Model Number VSOEPC1 0-5 0-100 (Parker Hannifin Corporation, Hollis, N.H.).

As to other particular embodiments of the invention, the control fluid controller (19) can be part of a microfluidic instrument (176) such as a liquid chromatograph (23) or a flow cytometer (24). With respect to certain flow cytometers (24), such as the Beckman Coulter MOFLO SX® or MOFLO XDP®, the control fluid controller (19) can be a gas pressure controller (27) of the flow cytometer (24) which conventionally operates to establish and maintain a gas pressure within one or more sheath fluid tank(s) for the delivery of sheath fluid (8) to the flow cytometer (24) or within a particle source for delivery of a sample fluid containing a plurality of particles to the flow cytometer (24). The gas pressure controller (27) of a flow cytometer (24) can be modified and programmed for utilization as described below.

Figure 2:
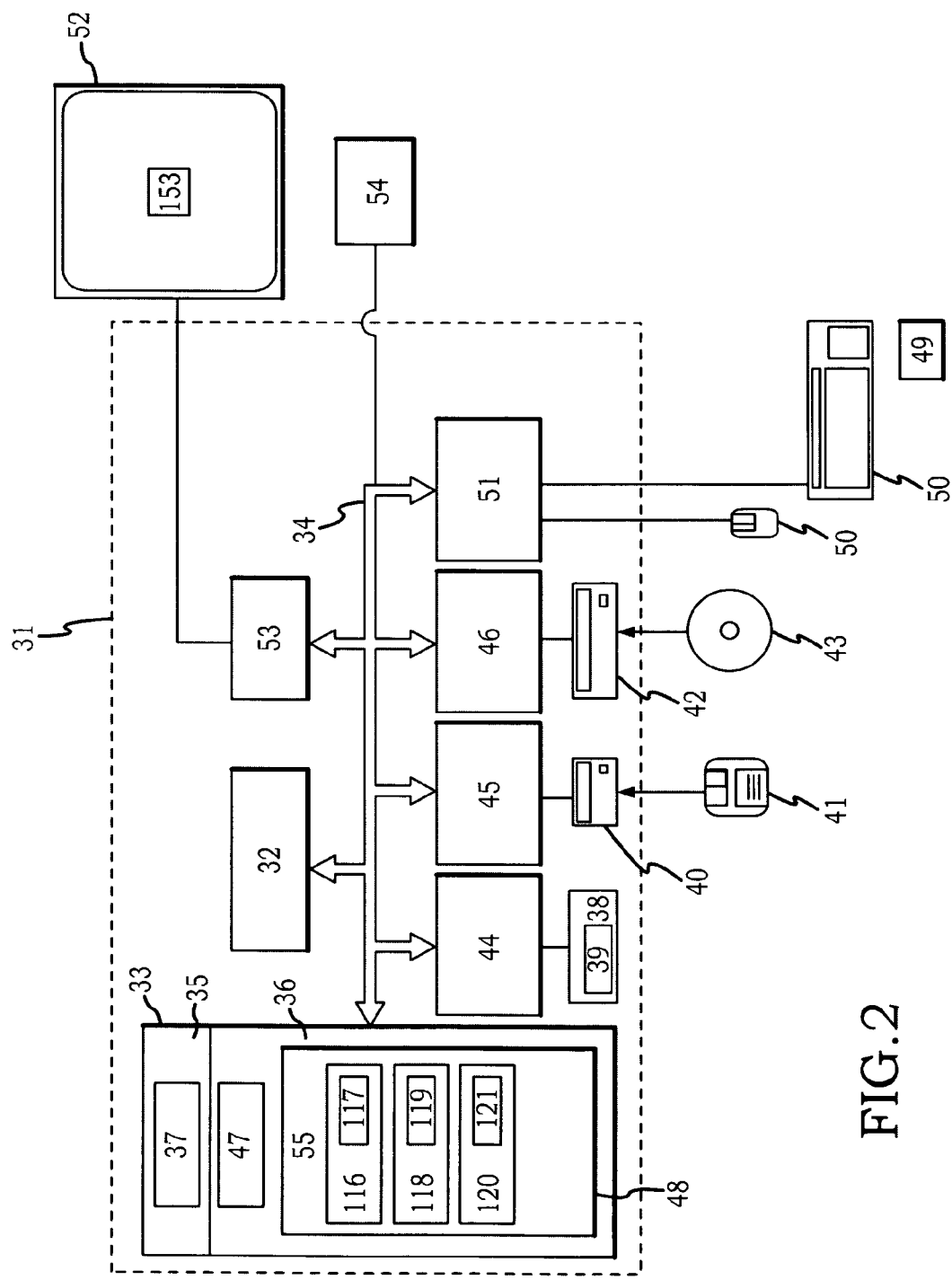

Now referring primarily to FIGS. 1 and 2, embodiments of the invention can further include a computer (31). The computer having at least one processing unit (32), a memory element (33), and a bus (34) which operably couples components of the computer (31), including, without limitation the memory element (33) to the processing unit (32). The computer (31) may be a conventional computer, a distributed computer, or any other type of computer which may contain all or a part of the elements described or shown to accomplish the functions described herein; the invention is not so limited. The processing unit (32) can comprise without limitation one central-processing unit (CPU), or a plurality of processing units which operate in parallel to process digital information, or a digital signal processor (DSP) plus a host processor, or the like. The bus (34) can be without limitation any of several types of bus configurations such as a memory bus or memory controller, a peripheral bus, and a local bus using any of a variety of bus architectures. The memory element (33) can without limitation be a read only memory (ROM) (35) or a random access memory (RAM) (36), or both. A basic input/output system (BIOS) (37), containing routines that assist transfer of data between the components of the computer (31), for example during start-up, can be stored in the memory element (33). The computer (31) can further include a hard disk drive (38) for reading from and writing to a hard disk (39), a magnetic disk drive (40) for reading from or writing to a removable magnetic disk (41), and an optical disk drive (42)

for reading from or writing to a removable optical disk (43) such as a CD ROM or other optical media which for brevity are not described in detail as each sufficiently described for a person of ordinary skill in the art to make and use the numerous and varied embodiments of the invention.

The hard disk drive (38), magnetic disk drive (40), and optical disk drive (42) can be connected to the bus (34) by a hard disk drive interface (44), a magnetic disk drive interface (45), and an optical disk drive interface (46), respectively. The drives and their associated computer-readable media can provide nonvolatile storage of computer-readable instructions, data structures, program modules and other data for the computer (31). It can be appreciated by those skilled in the art that any type of computer-readable media that can store data that is accessible by a computer, such as magnetic cassettes, flash memory cards, digital video disks, Bernoulli cartridges, random access memories (RAMs), read only memories (ROMs), or the like, may be utilized in embodiments of the invention.

The computer (31) can further include an operating system (47) and a control fluid controller application (48) which can be stored on or in the hard disk (39), magnetic disk (40), optical disk (42), or memory element (33) or alternately the functionalities of the control fluid controller application (48) may be implemented as an application specific integrated chip (ASIC) or file programmable gate array (FPGA), or the like. The control fluid controller application (48) loaded onto the computer (31) produces a machine, such that the instructions which execute on the computer (31) or other programmable data processing apparatus implement the functions specified in the flowchart block or blocks shown in the figures and further described herein.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware based computer systems which perform the specified functions or steps, or suitable combinations of special purpose hardware and computer instructions.

It should be appreciated that the particular implementations shown and described herein are illustrative of the invention and its best mode and are not intended to otherwise limit the scope of the present invention in any way. Indeed, for the sake of brevity, conventional data networking, application development and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical data encoding-decoding system.

A computer user (49) can enter commands and information into the computer (31) through input devices (50) such as a keyboard and a pointing device such as a mouse. Other input devices (50) may include a microphone, joystick, game pad, satellite dish, scanner, or the like. These and other input devices (50) are often connected to the processing unit (32) through a serial port interface (51) that can be coupled to the bus (34), but may be connected by other interfaces, such as a parallel port, game port, or a universal serial bus (USB). A monitor (52) or other type of display device can also be connected to the bus (34) via interfaces such as a video adapter (53), or the like. In addition to the monitor (52), the computer (31) can further include peripheral output devices (54), such as speakers and printers.

A "click event" occurs when the computer user (49) operates at least one function of the control fluid controller application (48) or other program or other application function, through an action or the use of a command which for example can include pressing or releasing a mouse button while a pointer element is located over a control icon displayed on the monitor (52). However, it is not intended that a "click event" be limited to the press and release of the button on a mouse while a pointer element is located over a control icon. Rather, the term "click event" is intend to broadly encompass any action or command by the computer user (49) through which a function of the operating system (47) or control fluid controller application (48), or other program or application is activated or performed, whether through clickable selection of one or a plurality of control icon(s) or by computer user (49) voice command, keyboard stroke(s), mouse button, touch screen, touch pad, or otherwise.

While the computer (31) shown in FIG. 1 can be utilized to practice the invention including the best mode, it is not intended that the description of the best mode of the invention or any preferred embodiment of the invention be limiting with respect to the utilization of a wide variety of similar, different, or equivalent computer means or network means to practice embodiments of the invention which include without limitation hand-held devices, such as personal digital assistants or camera/cell phone, multiprocessor systems, microprocessor-based or programmable consumer electronics, network PCs, minicomputers, mainframe computers, PLCs, or the like.

Again referring primarily FIGS. 1 and 2, as to particular embodiments of the invention the computer (31) and the control fluid controller application (48) and the control fluid controller (19) can be a part of a microfluidic instrument (176) such as an high pressure liquid chromatograph (23) or flow cytometer (24) such as a REFLECTION™ or a MOFLO® flow cytometer, MOFLO® SX flow cytometer, or MOFLO® XDP flow cytometer; however, these specific examples are not intended to be limiting with respect to the numerous and varied kinds of microfluidic instruments (176), liquid chromatographs (23) or flow cytometers (24) which can include the computer (31) having software applications (55) which can be utilized to activate the functions of a control fluid controller (19) to allow intermittent or continuous delivery of the control fluid (57) (such as amount of compressed gas (15) or an amount of compressed liquid (16)) from the control fluid source (14) as above described.

As to other embodiments of the invention, the computer (31) can be separate from the microfluidic instrument (176) such as those above-described, and can be loaded with the control fluid controller application (48). The control fluid controller application (48) loaded on the computer (31) can be executed to implement the functions of the control fluid controller (19) to regulate intermittent or continuous delivery of the control fluid (57) (whether an amount of compressed gas (15) or an amount of compressed liquid (16)) from the control fluid source (14). Alternately, the computer (31) loaded with the control fluid controller application (48) and the control fluid controller (19) can be one piece or one unit.

Now referring primarily to FIGS. 1 and 3-8, embodiments of the invention can further include a fluid flow characteristic regulator (58). The fluid flow characteristic regulator (58) can operate to receive a fluid flow (11) of an amount of fluid (7) from the fluid source (1) (regardless of the kind of fluid flow generator (10) utilized to generate the fluid flow (11)). The fluid flow (11) received by the fluid flow characteristic regulator (58) can have one or more fluid flow characteristics (59). The term "fluid flow" as to embodiments of the invention can include a continuous or a variable or an intermittent flow of an amount of fluid (2) from the fluid source (1) without limitation on volume, rate, pressure, duration, or the like. The fluid flow (11) with respect to certain applications may be intermittent with the fluid flow (11) having a range between zero and a particular flow rate value or may be variable within the practical operating limits of a particular instrument such as an high pressure liquid chromatograph (23) or flow cytometer (24) or may be continuous with lesser or greater variation in a particular one of the fluid flow characteristics (59); however, the term "fluid flow" is not intended to be limited by these particular examples. The term "fluid flow characteristic(s)" as to embodiments of the invention means one fluid flow characteristic (59) or a combination of fluid flow characteristics (59) of a fluid flow (11) at least one of which can be regulated or altered within the fluid flow characteristic regulator (58). The one or more fluid flow characteristics (59) of a fluid flow (11) that can be regulated or altered within the fluid flow characteristic regulator (58) can be fluid flow temperature, fluid flow pressure, fluid flow rate, amplitude or frequency of a fluid pressure waveform, amplitude or frequency of a fluid temperature waveform, amplitude or frequency of a fluid flow rate waveform. However, this list of particular fluid flow characteristics (59) is not meant to be limiting with regard the fluid flow characteristics (59) which can be regulated or altered within the fluid flow characteristic regulator (58). As one non-limiting example, the fluid flow generator (10) may generate pulsation in the fluid flow (11) received by the fluid flow characteristic regulator (58), the pulsation having a particular wave form(s) of particular frequency and amplitude. The fluid flow characteristics (59) of the pulsation in the fluid flow (11) can be regulated or altered within the fluid flow characteristic regulator (58), as below described. Specifically, fluid flow characteristics (59) can include the pressure wave form and flow rate waveform (variation in fluid flow pressure or fluid flow rate) generated by operation of a dual piston liquid chromatography pump (12) such as a Jasco Intelligent HPLC Pump Model Number PU-2086 or 2087, Jasco Corporation, 2967-5, Ishishkwawa-cho, Hachioji, Tokyo, Japan. Additionally, the actual level of at least one fluid flow characteristic (59) can be assessed or measured for comparison with a pre-determined level (or desired level) of the same at least one fluid flow characteristic (59), as described below.

Again referring primarily to FIGS. 1, and 3-8, embodiments of the fluid flow characteristic regulator (58) can have a configuration which defines an internal chamber (60). The internal chamber (60) of the fluid flow characteristic regulator (58) can have a configuration which defines a fluid flow path (61) in which an amount of fluid (2) received from the fluid source (1) flows between a fluid flow inlet (62) and a fluid flow outlet (63) (fluid flow (11)). The internal chamber (60) of the fluid flow characteristic regulator (58) further defines a control fluid flow path (64) in which an amount of control fluid (57) received from the control fluid source (14) flows between a control fluid inlet (65) and a control fluid outlet (66) (control fluid flow (20). In general, embodiments of the fluid flow characteristic regulator (58) are configured to provide a fluid flow path (61) and a control fluid path (64) located within the fluid flow characteristic regulator (58) which allows one or more of the fluid flow characteristics (59) of the fluid flow (11) to be responsive to one or more of the control fluid flow characteristics (67) of the control fluid flow (20) as the amount of control fluid (57) flows between the control fluid inlet (65) and the control fluid outlet (66) and the amount of fluid (2) flows between the fluid flow inlet (62) and the fluid outlet (63).

Certain embodiments of the invention may only have a control fluid inlet (65) coupled to the fluid flow characteristic regulator (58) with the control fluid path (64) being closed end. In these embodiments, the control fluid outlet (66) can comprise a pressure release valve, or drain valve, a bleed valve, or the like, coupled to fluid flow characteristic regulator (58) or to the control fluid controller (19) regulated by the control fluid controller (19) to maintain a desired level of at least one control fluid characteristic (67).

Again referring primarily to FIG. 1, embodiments of the fluid flow characteristic regulator (58) can further include a flexible barrier (68) which fluidicly isolates the fluid flow path (61) from the control fluid flow path (64). As a non-limiting example, the embodiments of the invention shown in FIGS. 1 and 3-8 utilize a flexible barrier (68) comprising a substantially planar sheet of flexible material having a thickness which disposes a first barrier surface (69) and a second barrier surface (70) in substantially opposed planar relation. The first flexible barrier surface (69) in part defines the configuration of the fluid flow path (61) and the second flexible barrier surface (70) in part defines the configuration of the control fluid flow path (64). The first flexible barrier surface (69) engages the fluid flow (11) in part or in the entirety along the distance of the fluid flow path (61) between the fluid flow inlet (62) and the fluid flow outlet (63). The second barrier surface (70) engages the control fluid flow (20) in part or in the entirety along the distance of the control fluid flow path (64) between the control fluid inlet (65) and the control fluid outlet (66) (or as to those embodiments which only provide a control fluid inlet (65) the second barrier surface). Typically, the flexible barrier (68) will be configured from an inelastic flexible material substantially impermeable to the fluid flow (11) and the control fluid flow (20) within the fluid flow characteristic regulator (58) and which can deformed or displaced without any substantial stretching to a lesser or greater extent in response to the load exerted on either the first barrier surface (69) or the second barrier surface (70) by the fluid flow (11) or the control fluid flow (20). As to certain embodiments, the flexible barrier (68) does not store sufficient energy from receiving the load to return to its original shape. Rather, the flexible barrier (68) can be made of an inelastic flexible material which deforms or displaces away from the fluid flow (11) or the control fluid flow (20) whichever exerts the greater pressure. By providing an inelastic flexible material as above described, the flexible barrier (68) does not resist the load exerted by the fluid flow (11) or the control fluid flow (20) but deforms based upon the relative loading to alter the configuration of the fluid flow path (61) or the control fluid flow path (64). Without limiting the forgoing, the flexible barrier (68) of an inelastic flexible material can be generated from a low density polyethylene.

Figure 4:
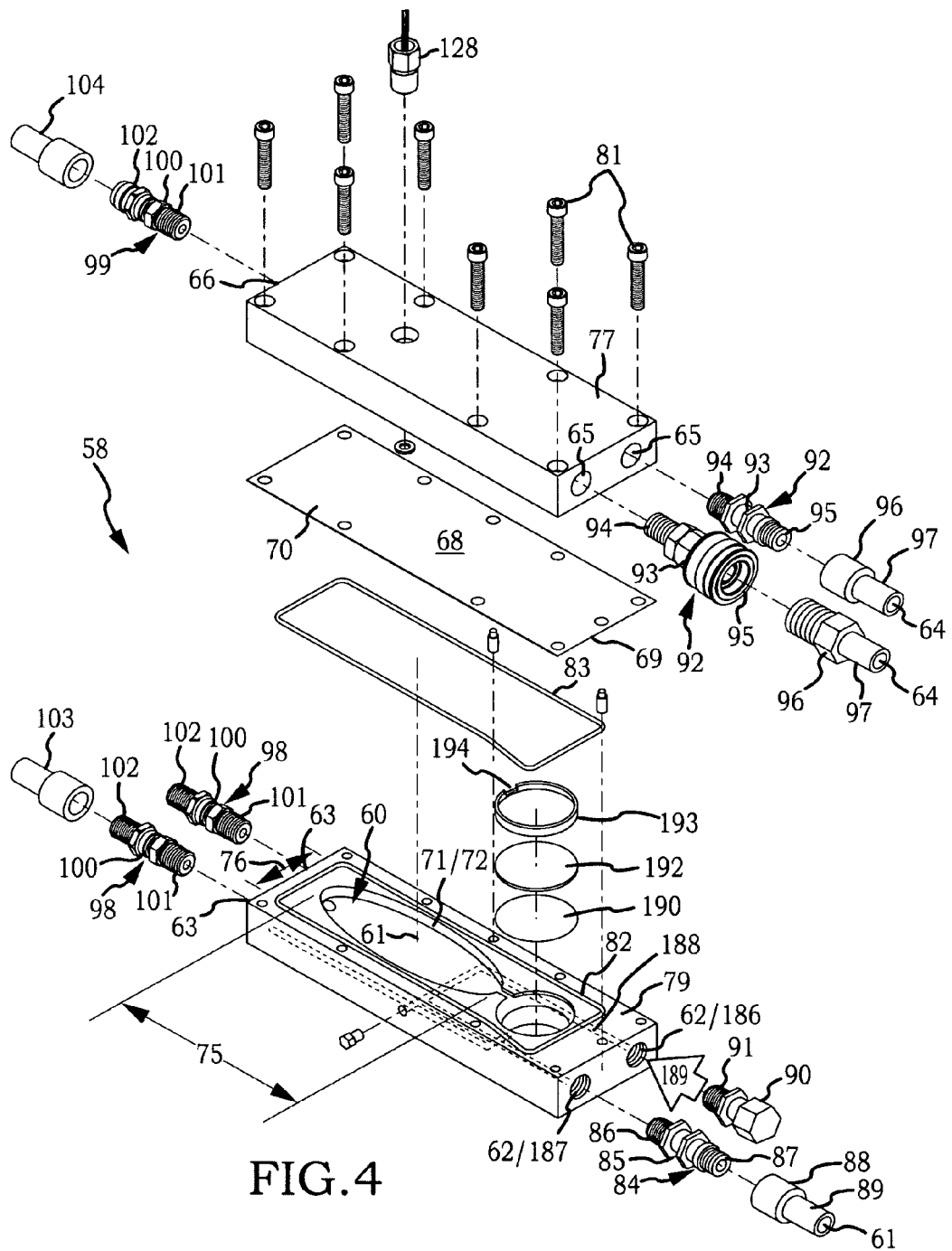
FIG. 4 is an exploded view of a particular embodiment of a fluid flow characteristic regulator.

Now referring to FIGS. 1 and 4, a particular non-limiting embodiment of the fluid flow characteristic regulator (58) provides an internal chamber (60) which includes a fluid flow path (61) having between the fluid flow inlet (62) and the fluid flow outlet (63) a volume of between about 15 milliliters ("mL") and about 35 mL and a control fluid flow path (64) of between about 100 mL and about 200 mL. As show in FIG. 4, the configuration of the control fluid flow path (64) and the configuration of fluid flow path (61) in plan view can be oval. Particular embodiments of the invention can provide each of the fluid flow path (61) and the control fluid flow path (64) with an oval constructional form in plan view having a length (75) in the range of about 5 inches to about 9 inches and a width (76) in the range of about 1 inch to about 3 inches. The side wall (71) of the fluid flow path (61) in the oval constructional form can be substantially vertical having a height (72) in the range of between about one-sixteenth of an inch and about three eighths of an inch. The side wall (73) of the control fluid flow path (64) in the oval constructional form can be substantially vertical having a height (74) in the range of between about one-half inch and about one inch. These particular volume and dimensional relations between the fluid flow path (61) and the control fluid flow path (64) are not intended to be limiting but are intended to provide sufficient description from which the person of ordinary skill in the art can make an use a numerous and wide variety of embodiments of the fluid flow characteristic regulator.

Again referring primarily to FIGS. 1 and 4, another non-limiting embodiment of the fluid flow characteristic regulator (58) configured for utilization with high performance liquid chromatographs (23) or flow cytometers (24) can provide the fluid flow path (61) and the control fluid flow path (64) having an oval constructional form in plan view of about seven and one-quarter inches in length (75) and about three and one-quarter inches in width (76). The side wall (71) of the oval constructional form of the fluid flow path (61) being substantially vertical and having a height (72) of about one-eighth inch and the side wall (73) of the control fluid flow path (64) having a height (74) of about three-quarters inch. The volume of the fluid flow path (61) of this particular configuration being about 25 milliliters and the volume of the control fluid flow path (64) being about 180 milliliters. Again, the dimensional relations are not intended to be limiting but to provide sufficient guidance of one of ordinary skill in the art to make a numerous and wide variety of embodiments of the fluid flow characteristic regulator (58) which can have a fluid flow path (61) and control fluid flow path (64) which may be of similar constructional form or substantially different constructional form for example cylindrical, rhombus, rectangular, or the like.

Now referring primarily in FIGS. 1 and 4, the flexible barrier (68) can be sealably engaged between a first regulator portion (77) having an internal surface (78) which defines the configuration of control fluid path (64) and a second regulator portion (79) having an internal surface (80) which defines the configuration of the fluid flow path (61). Sealable engagement of the flexible barrier (68) between the first regulator portion (77) and the second regulator portion (79) can be achieved by use of a plurality of mechanical fasteners (81) which operate to sufficiently urge the surfaces of the flexible barrier (68) against the corresponding surfaces of the first regulator portion (77) and the second regulator portion (79). While the plurality of mechanical fasteners (81) utilized with the embodiment of the invention shown in FIG. 3 comprise a plurality of spirally threaded fasteners such as Allen head screws; the invention is not so limited and the mechanical fasteners (81) can be for example bolts with nuts with spirally mated threads, compression clamps, or the like. As to certain embodiments of the fluid flow characteristic regulator (58), a first seal element (82) can be located between the engaged surfaces of the second regulator portion (79) and the corresponding engaged surface of the flexible barrier (68). Similarly, a second seal element (83) can be located between the engaged surfaces of the first regulator portion (77) and the corresponding engages surface of the flexible barrier (68).

Again referring primarily to FIG. 4, the embodiment of the fluid flow characteristic regulator (58) shown provides a pair of fluid flow inlets (62) and a pair fluid flow outlets (63); however, the invention is not so limited. As to particular embodiments of the invention, one fluid flow inlet (62) and one fluid flow outlet (63) can be provided, or one fluid flow inlet (62) and two fluid flow outlets (63) can be provided, or two fluid flow inlets (62) and one fluid outlet (63) can be provided, or a greater or lesser number of fluid flow inlets (62) or fluid flow outlets (63) can be provided in various permutations or combinations depending upon the application.

Figure 3:
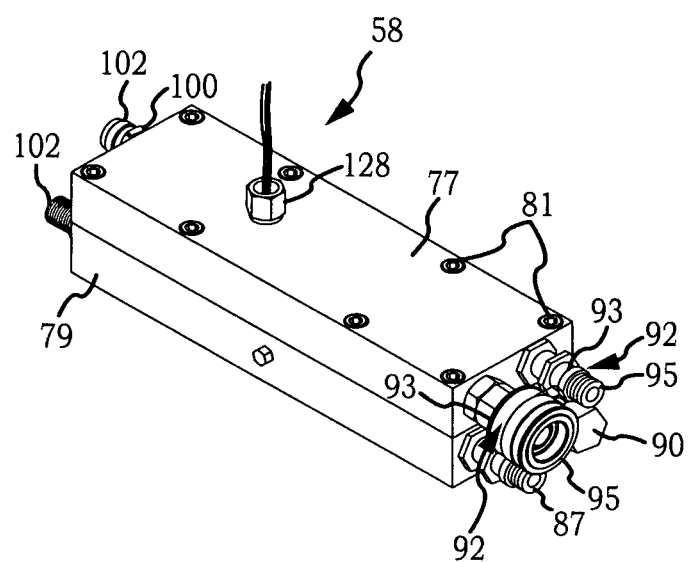
FIG. 3 is a perspective view of a particular embodiment of a fluid flow characteristic regulator.

Similarly, the particular embodiment of the fluid flow characteristic regulator (58) shown in FIG. 3 provides a pair of control fluid flow inlets (65) and a pair control fluid flow outlets (66); however, the invention is not so limited. As to particular embodiments of the invention, one control fluid flow inlet (65) and one control fluid flow outlet (66) can be provided, or one control fluid flow inlet (65) and two control fluid flow outlets (66) can be provided, or two control fluid flow inlets (65) and one control fluid outlet (66) can be provided, or a greater or lesser number of control fluid flow inlets (65) or control fluid flow outlets (66) in various permutations or combinations depending upon the application.

Now referring specifically to FIG. 4, as to certain embodiments of the fluid flow characteristic regulator (58), the pair of fluid flow inlets (62) can be utilized as a temperature control fluid inlet (186) and a temperature control fluid outlet (187) having a temperature control fluid path (188) (in broken lines) disposed between in which a temperature control fluid (189) can flow to regulate the temperature of the fluid flow characteristic regulator (58). The pair of fluid flow outlets (63) can correspondingly function as a fluid flow inlet (62) and a fluid flow outlet (63) of the fluid flow path (61).

Particular embodiments of the fluid flow characteristic regulator (58), can further include a fluid flow filter (190). The fluid flow filter (190) as shown in FIG. 4 can have a circular configuration; however, the invention is not so limited. The second regulator portion (79) can have a configuration which sealably engages proximate the filter perimeter (191). Sealable engagement of the fluid flow filter (190) with the second regulator portion (79) results in fluid flow (11) which passes through the fluid flow filter (190) prior to entry into the fluid flow path (61) of the fluid flow characteristic regulator (58) which can remove pathogens and particles from the fluid flow (11). Embodiments of the fluid flow filter (190), can have two micrometer pores. As a non-limiting example, a suitable fluid flow filter (190) can be obtained from Meissner Filtration Products, Inc. Part No. SM0.2-25-1S having a circular configuration with an active filter area of about four square centimeters. The second regulator portion (79) can be further configured to receive a frit (192) of porous plastic or glass which can be located adjacent the fluid flow filter (190) to provide support for the fluid flow filter (190). The fluid flow (11) can pass through the fluid flow filter (190) and the adjacent frit (192) prior to entry into the fluid flow path (61). A spacer element (193) can disposed between the frit (192) and the first barrier surface (69). Sealable engagement of the first regulator portion (77) and the second regulator portion (79) with the corresponding portions of the opposed first barrier surface (69) and the second barrier surface (70) can also produce sealable engagement of the first barrier surface (69) with the corresponding surfaces of the spacer element (193). The spacer element (193) can further include a spacer outlet (194) through which the filtered fluid flow (11) passes to enter the fluid flow path (61) of the fluid flow characteristic regulator (58).

Again referring primarily to FIG. 4, the embodiment of the fluid flow characteristic regulator (58) shown further provides a fluid flow inlet adapter (84) having an adaptor body (85) having a first adapter end (86) having a spiral thread for rotatable engagement with a mated spiral thread of the fluid flow inlet (62) of the second regulator portion (79). The fluid flow inlet adapter body (85) having a second adapter end (87) having a spiral thread for rotatable engagement with a mated spiral thread of a fluid flow conduit adapter (88) of a fluid flow conduit (89) which provides a fluid flow path (61) between the fluid flow generator (10) and the fluid flow characteristic regulator (58). While the fluid flow inlet adapter body (85) shown in FIG. 4 shows the first adapter end (86) and the second adapter end (87) having a spiral thread; the invention is not so limited, and any manner of engagement between the fluid flow inlet (62) and the fluid flow inlet adapter (84) which provides a substantially fluid tight seal can be utilized including a weld, spin weld, compression fitting, mated spiral threads, quick disconnect fittings, or the like. As to certain embodiments of the fluid flow characteristic regulator (58), the second regulator portion (79) of the fluid flow characteristic regulator (58) may have two or more fluid flow inlets (62) and only one fluid flow inlet (62) may be used in a particular application with the other fluid flow inlets (62) engaged with a plug element (90) having a plug end (91) including as a non-limiting example, a spiral thread for rotatable engagement with the unused fluid flow inlets (62).

Similarly, the embodiment of the fluid flow characteristic regulator (58) shown in FIG. 4 further provides a control fluid flow inlet adapter (92) having an adaptor body (93) having a first adapter end (94) having a spiral thread for rotatable engagement with a mated spiral tread of the control fluid flow inlet (65) of the first regulator portion (77). The control fluid flow inlet (65) adapter body (93) has a second adapter end (95) which can have a spiral thread for rotatable engagement with a mated spiral thread of a control fluid flow conduit adapter (96) of a control fluid flow conduit (97) which provides a control fluid flow path (64) between the air pressure controller (19) and the fluid flow characteristic regulator (58). While the control fluid flow inlet (65) adapter bodies (93) shown in FIG. 4 provide a first adapter end (94) and a second adapter end (95) having a spiral thread; the invention is not so limited and any manner of engagement between the control fluid flow inlet (62) and the control fluid flow inlet adapter (92) which provides a substantially fluid tight seal can be utilized including a weld, spin weld, compression fitting, mated spiral threads, or the like. As to certain embodiments of the fluid flow characteristic regulator (58), the first portion (77) of the fluid flow characteristic regulator (58) may have two or more control fluid flow inlets (62) and only one control fluid flow inlet (62) may be used in a particular application with the other control fluid flow inlets (62) engaged with a plug element (90) having a plug end (91) including a spiral thread (or other configuration matable with the control fluid inlet (62)) for rotatable engagement with the unused fluid flow inlets (62).

Again referring to FIG. 4, embodiments of the a fluid flow characteristic regulator (58) can similarly include one or more fluid flow outlet adapters (98) and the one or more control fluid outlet adapters (99) each having a corresponding adaptor body (100) having corresponding first adapter end (101) and second adapter end (102) having a similar numerous and wide variety of constructional forms which allow substantially fluid tight engagement with one or more of the fluid flow outlets (63) and one or more of the control fluid flow outlets (66) and substantially fluid tight engagement with one or more corresponding fluid flow outlet conduits (103) or one or more control fluid outlet conduits (104).

Now referring primarily to FIG. 1, particular embodiments of the invention can further include one or more fluid flow variation sensor(s) (105) each of which function to generate a fluid flow variation signal (106) which varies based upon sensed variation in the fluid flow (11) in the fluid flow path (61) within the fluid flow characteristic regulator (58). Variation in the fluid flow (11) in the fluid path (61) within the fluid flow characteristic regulator (58) can include as non-limiting examples variation in fluid flow volume of the fluid flow (11), variation in height of the fluid flow (11) in the fluid flow path (61), variation in temperature of the fluid flow (11), variation in pressure of the fluid flow (11), or the like.

Again referring primarily to FIG. 1, as to the particular non-limiting embodiment of the invention shown, the fluid flow variation sensor (105) can function to generate a fluid flow variation signal (106) which varies based upon sensed movement (107) of the flexible barrier (68). The flexible barrier (68) can move in response to variation in the fluid flow (11) in the fluid flow path (61) which engages the first barrier surface (69). Movement of the flexible barrier (68) includes movement, displacement, travel, flexure, deformation, positional change, or the like.

Now referring primarily to FIGS. 1 and 2, a non-limiting example of a fluid flow variation sensor (105) which can generate a fluid flow variation signal (106) based upon sensed movement (107) of the flexible barrier (68) includes a Hall Effect sensor (108). Hall Effect sensors (108) consume a small amount of electrical current (109) and when consuming current, their electrical resistance (110) can be changed by magnetic field forces (111). The variation in polarity and strength of the magnetic field (111) can correspondingly generate variation in the electrical resistance (110) in the Hall Effect sensor (108) and a corresponding difference between the ingoing voltage (112) and the out going voltage (187) of a Hall Effect sensor (108) can be converted from an analog signal (113) to a digital signal (114) by an analog to digital converter (115). The resulting digital signal (114) can be received and assessed by the control fluid controller application (48) (see FIG. 2) served by the computer (31). In part, the control fluid controller application (48) provides a fluid flow variation signal analyzer (116) which functions to receive and analyze the digital signal (114) and generates continuous stream of voltage variation values (117) which correspond to the difference between the ingoing voltage (112) and the out going voltage (187) of the Hall Effect sensor (108). The control fluid controller application (48) can further provide a voltage variation value matching element (118) which functions to receive voltage variation values (117) and further functions to continuously or intermittently match the voltage variation values (117) with corresponding control fluid adjustment values (119). The control fluid adjustment values (119) can include depending upon the embodiment of the invention gas pressure adjustment values, gas volume adjustment values, gas delivery rate values, or the like, A control fluid delivery adjustment element (120) can function to receive control fluid adjustment values (119) and further functions in response to generate continuously or intermittently control fluid delivery adjustment values (121) receivable by the control fluid controller (19). Based on received control fluid delivery adjustment values (121), the control fluid controller (19) operates to intermittently or continuously adjust control fluid characteristics (67) (volume, pressure, rate, temperature, or the like) of the amount of control fluid (57) delivered from the control fluid source (14). The amount of control fluid (57) having control fluid characteristics (67) adjusted by the control fluid controller (19) can be received by the control fluid flow path (64) within the first regulator portion (77) to act directly upon the fluid flow (11) in the fluid flow path (61) or indirectly act upon the fluid flow (11) in the fluid flow path (61) by acting upon the flexible barrier (68).

As to certain embodiments, the control fluid (57) can be an amount of gas (15) regulated at constant gas pressure by the control fluid controller (19) such that the fluid flow (11) in the fluid flow path (61) is held at a constant flow rate by displacement of the flexible barrier (68). As the fluid flow (11) generated by displacement of flexible barrier (68) exhausts the amount of fluid in the fluid flow path (61), the sensed displacement of the flexible barrier (68) by the fluid flow variation sensor (105) results in generation of voltage variation values (117) which can be utilized to regulate operation of a high pressure liquid chromatography pump (12) (or other pump) to refresh the amount of fluid in the flow path (61) of the fluid flow characteristic regulator (58). In this manner, fluid flow (11) from the fluid flow characteristic regulator (58) can have a constant flow rate, while the incoming fluid flow (11) entering the fluid flow characteristic regulator (58) into fluid flow path (61) can have a variable fluid flow (11) corresponding the operation of the high pressure liquid chromatography pump (12).

Again referring primarily to FIG. 1, as to those particular embodiments of the invention which include a Hall Effect sensor (108) and a flexible barrier (68), the Hall Effect sensor (108) can be mounted on the second barrier surface (70) of the flexible barrier (68) or on the internal surface (78) of the first regulator portion (77) (or can be fixed to a support extending from the internal surface (78) of the first regulator portion (77) toward the flexible barrier (68)) depending on the application. A magnetic material (122) capable of generating sufficient magnetic field forces (111) to alter electrical resistance (110) of the Hall Effect sensor (108) can be mounted on the second barrier surface (70) of the flexible barrier (68) or on the internal surface (78) of the first regulator portion (77) (or can be fixed to a support extending from the internal surface (78) of the first regulator portion (77) toward the flexible barrier (68)). The magnetic material (122) and the Hall Effect sensor (108) as to the particular embodiment can be mounted in opposed relation a distance apart (123), As the flexible barrier (68) moves in response to the control fluid flow (20) within the control fluid flow path (64), the distance (123) between the magnetic material (122) and the Hall Effect sensor (108) correspondingly increases or decreases with a corresponding increase or decrease in the electrical resistance (110) of the Hall Effect sensor (108) and a corresponding increase of decrease in voltage (112) as above described. The fluid flow variation signal (106) can be can be carried the computer (31) or other voltage indicator (126) as above described a signal circuit element (127). As to those embodiments of the invention without a flexible barrier (68), the Hall Effect sensor (108) can be mounted on the internal surface (78) of the first regulator portion (77) and the magnetic material (122) can further include a float (124) responsive to change in the height of the fluid flow (11) within the fluid flow path (61).

Now referring primarily to FIG. 1, embodiments of the invention can further provide a power source (124) and if necessary a power converter (125) (for example, to convert 120 volts alternating current to 4.5 volts direct current) and other electrical circuit elements (177) to provide electrical current (109) to the fluid variation sensor (105) (including those embodiments of the invention which include a Hall Effect sensor (108). The fluid flow characteristic regulator (58) can further provide a plug (128) having fluidicly sealable a passage through which electrical circuit elements (177) signal circuit elements (127) can pass.

Figure 9:
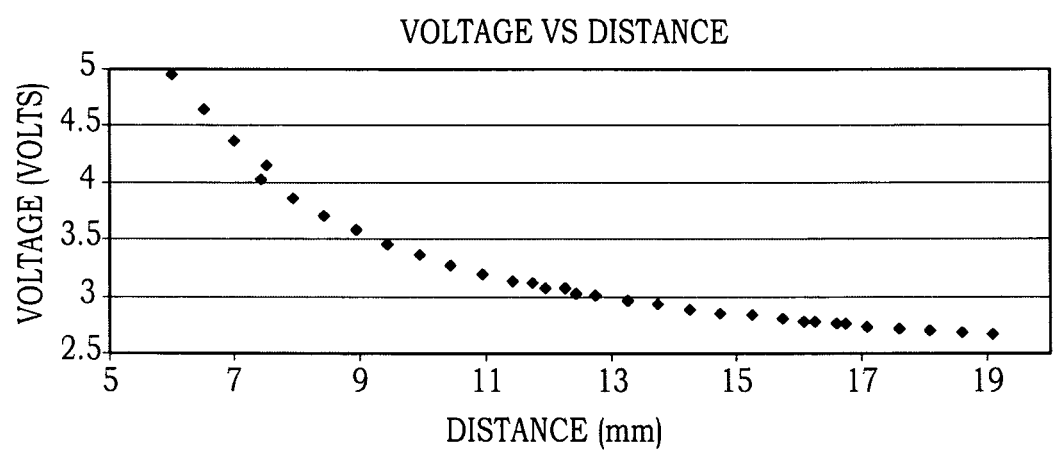
FIG. 9 is a graph which plots volts generated by a Hall Effect sensor over distance between the Hall Effect sensor and a magnetic field.

Now referring primarily to FIG. 9, which provides a plot of distance (178) between a magnetic material (122) and a Hall Effect sensor (108) and volts (112) generated by the Hall Effect sensor (108). As can be understood from the plot, the greater the distance from the magnetic material (122) (the weaker the magnetic forces (111)) the lesser the magnitude of the voltage (112) generated by the Hall Effect sensor (108). While particular examples of the invention are described utilizing a Hall Effect sensor (108), it is not intended to be limiting with respect to the wide variety of fluid flow variation sensor(s) (105) and temperature variation sensors (129) that can be used in alternate embodiments of the invention including without limitation light emitting diode distance measurement, ultrasonic distance measurement, optical distance measurement, fluid tapping, displacement sensors, micro-sized temperature sensors, or the like.

Figure 10:
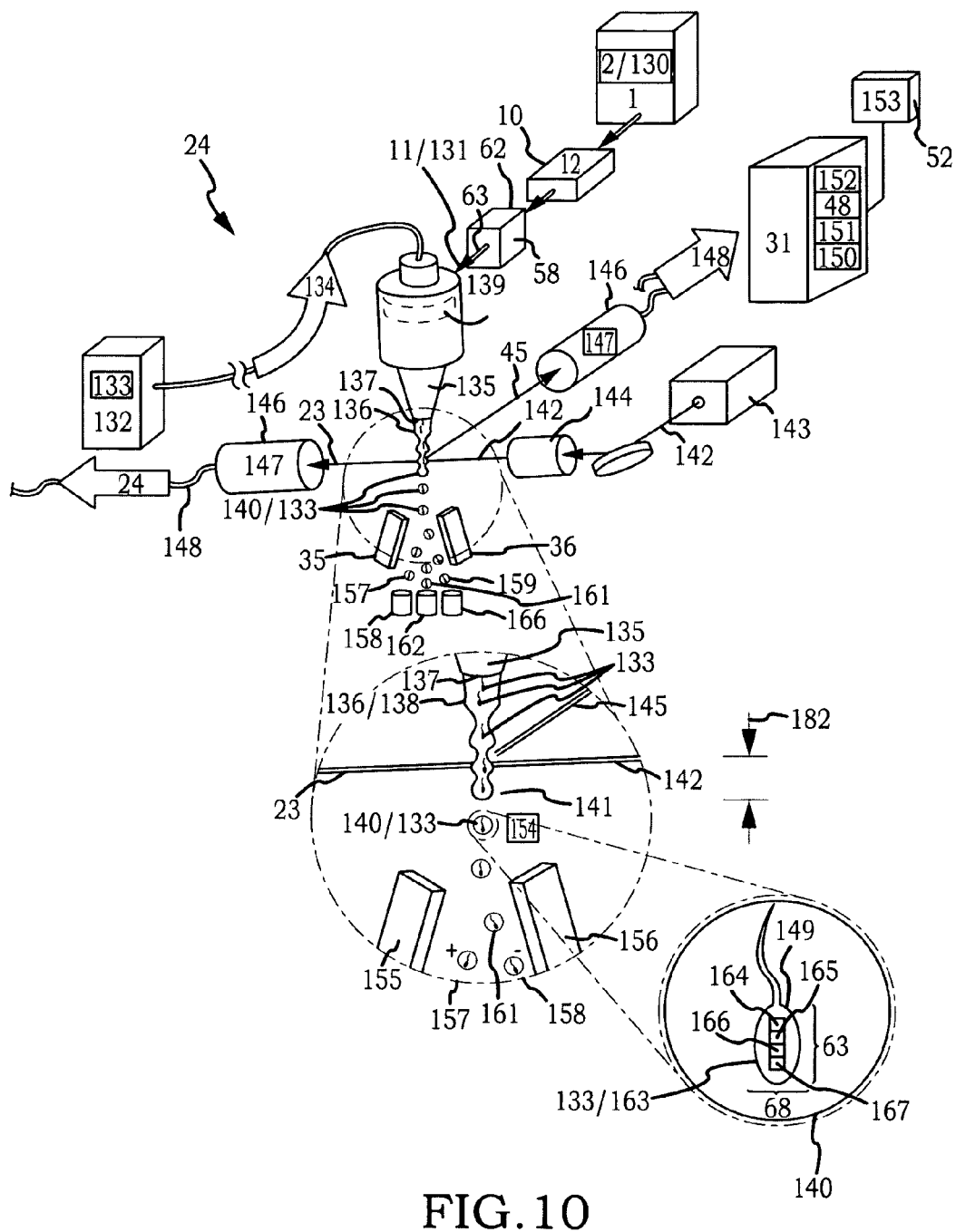
FIG. 10 is a block diagram of a particular embodiment of the invention which generates a regulated fluid flow delivered to a flow cytometer.

Now referring primarily to FIG. 10, certain embodiments of the fluid processing system which in part include the above described fluid flow characteristic regulator (58) can further include a flow cytometer (24). The flow cytometer (24) can be fluidicly coupled to the fluid flow outlet (63) of the fluid flow characteristic regulator (58). The fluid flow (11) from the fluid flow outlet (63) can comprise a sheath fluid stream (131). A particle source (132) can entrain a plurality of particles (133) in a sample fluid stream (134). The sample fluid stream (134) entraining a plurality of particles (133) joins the sheath fluid stream (131) in a nozzle (135) of the flow cytometer (24) as a coaxial laminar flow (136) with the sample fluid stream (134) surrounded by the sheath fluid stream (131). The coaxial laminar flow (136) exits a nozzle orifice (137) and can be established below the nozzle (135) as a fluid stream (138) entraining the plurality of particles (133).

The nozzle (135) can be made responsive to an oscillator (139) (see FIG. 10 broken lines). Oscillation of the nozzle (135) can perturb the fluid stream (8) to establish a steady state oscillation of the fluid stream (138). One non-limiting example of an oscillator (139) capable of perturbing the fluid stream (138) directly or indirectly by oscillation of the nozzle (135) can be a piezoelectric crystal. The oscillator (139) may have an adjustable oscillation frequency that can be adjusted to perturb the stream at different frequencies. Steady state oscillation of the fluid stream (138) can be established in a condition such that droplets (140) are formed and break away from a contiguous part of the fluid stream (138). When the fluid stream (138) is established in this steady state fashion, a stable droplet break-off point (141) can be generated.

The fluid stream (138) in steady state oscillation can be interrogated with one or more light beams (142) (such as one or more a laser beams emitted from a light emission source (143)). The one or more light beams (142) can pass through a beam shaping optics (144) to configure the shape of the light beams (142) and focus the light beams (142) on the fluid stream (138). An amount of light (145) emitted or reflected from one of the plurality of particles (133) in the interrogated fluid stream (138) can be received by one or more photoreceivers (146). The photoreceivers (146) convert amount of light (147) receive into a signal (148) (whether analog, analog converted to digital, or digital) which varies whether in frequency, amplitude, or both frequency and amplitude) based upon differences in at least one particle characteristic (149) among the plurality of particles (133). The plurality of particles (133) can be biological particles such as cells, sperm cells, organelles, chromosomes, deoxyribonucleic acids (DNA), ribonucleic acids (RNA), DNA fragments, RNA fragments, proteins, protein fragments, peptides, oligonucleotides, or the like, but can also include non-biological particles such as beads, styrene beads, or the like, or as mixtures of biological particles, mixtures of non-biological particles, or mixtures of biological and non-biological particles. The term "at least one particle characteristic" for the purposes of this invention means at least one part, component, or differentially modified part or component common to at least a portion of the plurality of particles (133) entrained in the fluid stream (134) which varies in kind or amount between the plurality of particles (133).

Now referring primarily to FIG. 10, the flow cytometer (24) can further include a computer (31) as above described which executes the functions of a particle analysis application (150) which in part provides a signal analyzer (151) which intermittently or continuously converts the signal (148) produced by interrogation of the fluid stream (138) into a data representation (152) of occurrence or detection of at least one particle characteristic (149) in the plurality of particles (133) interrogated. The data representation (152) can be continuously or intermittently displayed as a viewable data representation (153) (see for example FIGS. 12 and 13) on a monitor (52) (see FIG. 2) or updated upon elapse of a short interval of time such as 100 milliseconds.

Certain embodiments of the signal analyzer (151) can further function to establish parameters and timed events by which the plurality of particles (133) can be separated, parsed or divided based upon the presence, absence, or amount of the at least one particle characteristic (149). A flow cytometer (24) such as a MOFLO® SX can further separate or sort the plurality of particles (133) into, discreet sub-populations based upon variation of at least one particle characteristic (149). Subsequent to exiting the nozzle orifice (137), the fluid stream (138) can break into droplets (140) each of which can contain a corresponding one each of the plurality of particles (133). Based on the above-described analysis of each of the plurality of particles (133) in the fluid stream (138), the droplets (140) can be differentiated based on the at least one particle characteristic (149) and separated by applying a charge (154) (whether positive or negative) to each one of the droplets (140) analyzed and then deflecting the trajectory of each of the droplets (140) by passing the droplets (140) through a pair of charged plates (155) (156). The trajectory of the positively charged droplets (157) can be sufficiently altered for delivery to a first container (158) and the trajectory of the negatively charged droplets (159) can be sufficiently altered for delivery to a second container (160). Uncharged droplets (161) are not deflected and can be delivered to a third container (162) (or to a waste stream).

As a non-limiting example, the plurality of particles (133) can be a plurality of sperm cells (163) and the at least one particle characteristic (149) can be the amount of deoxyribonucleic acid ("DNA") (164) contained in each of the plurality of sperm cells (163). The amount of DNA (164) can vary based upon whether the particular one of the plurality of sperm cells (163) contains an X chromosome (165) or a Y chromosome (166). The X chromosome (165) contains a greater amount of DNA (164) than the corresponding Y chromosome (166) regardless of the male mammal from which the plurality of sperm cells (163) is obtained. The DNA (164) can be stained by exposure to an amount of stain (167) (for example, Hoescht 33342 dye or DNA minor groove binders such as bis-benzamides, oligocarboxamides, polyamides, peptide nucleic acids, locked nucleic acids, or the like) and in response to interrogation with a light beam (142) (such as a laser beam) can emit an amount of light (145). Sperm cells (163) which bear an X chromosome (165) typically emit a greater amount of light (145) than sperm cells (163) bearing a Y chromosome (166) because each X chromosome (165) contains a greater amount of stained DNA (164) than a Y chromosome (165). The photoreceiver (146) can convert the amount of emitted light (145) into a signal (148) which correspondingly varies based upon the difference in the amount of light (145) emitted by sperm cells (163) bearing an X chromosome (165) and sperm cells (163) bearing a Y chromosome (166) when passed through the light beam (142). With respect to the separation of a plurality of sperm cells (163), the separated sub-populations can include sperm cells (163) bearing an X chromosome (165) isolated in the first container (158) and sperm cells (163) bearing a Y chromosome (166) isolated in the second container (160). Sperm cells (163) can be obtained from any of a wide and numerous variety of male mammals including for example, a bovid, an ovis, an equid, a pig, a cervid, a canid, a felid, a rodent, a whale, a dolphin, a rabbit, an elephant, a rhinoceros, a primate, or the like, as well as from certain male non-mammal species such as a species of fish.

Figure 11:
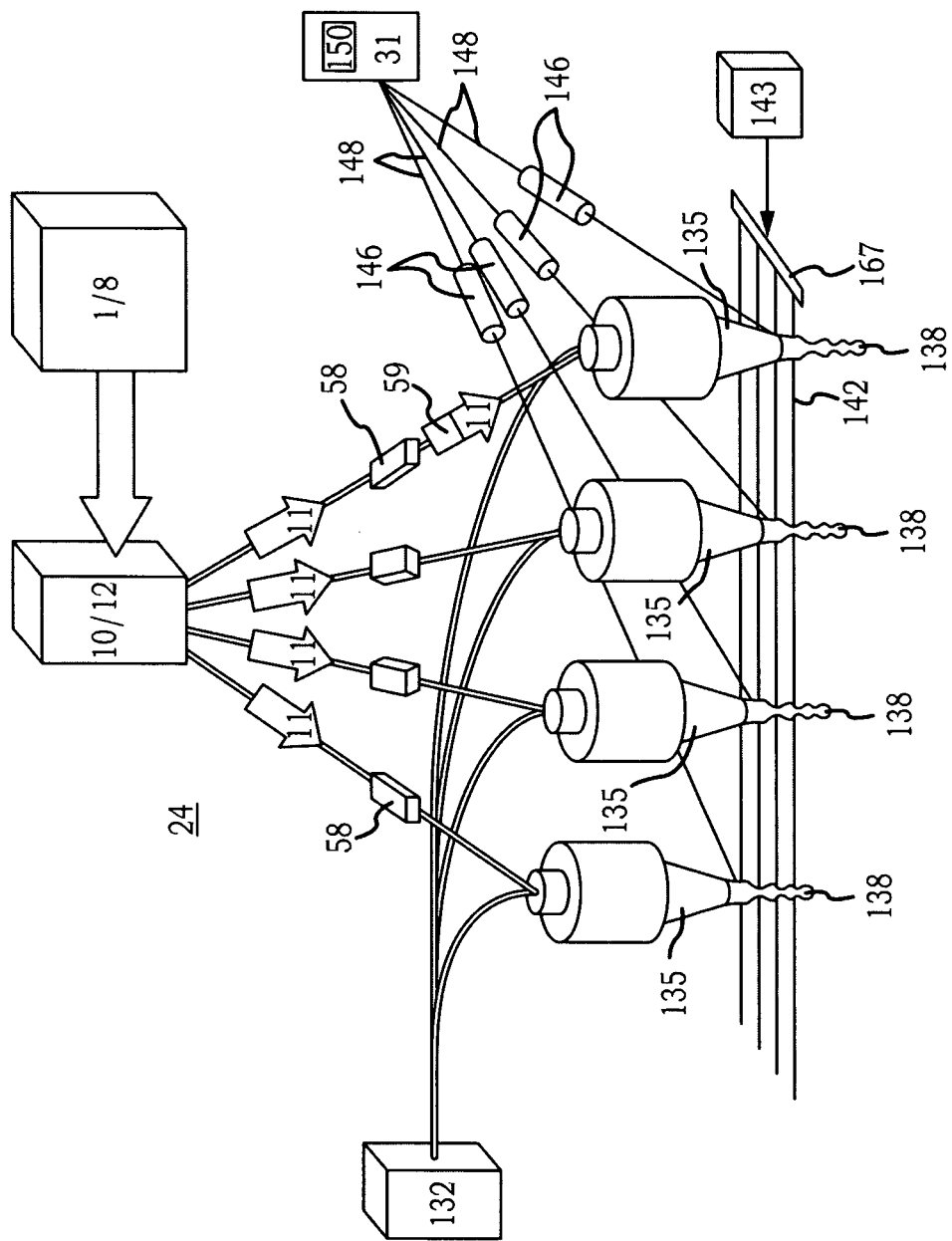
FIG. 11 is a block diagram of a particular embodiment of the invention which generates a regulated fluid flow delivered to a flow cytometer having a plurality of nozzles each of which can generate droplets in the fluid flow delivered from the corresponding nozzle orifice.

Now referring to FIG. 11, certain embodiments of the invention which include a flow cytometer (24) can utilize one fluid source (1) fluidicly coupled to one fluid flow generator (10) which in turn delivers a fluid flow (11) to a plurality of fluid flow characteristic regulators (58), as above described, each of which operate to maintain pre-determined fluid flow characteristics (59) in the fluid flow (11) delivered to a plurality of nozzles (135). The flow cytometer (24) can further utilize a common particle source (132) fluidicly coupled to a plurality of nozzles (135) (or can use a particle source (132) for each nozzle (135)). One light emission source (143) can generate a light beam (142) which can be split into a plurality of light beams (142) by use of a beam splitter (167). Each of the plurality of nozzles (135) can generate a fluid stream (138) which can be interrogated with one of the plurality of light beams (142). The amount of light (147) generated by interrogation of each fluid stream (138) can be received by a corresponding photoreceiver (146). The signal (148) from each photoreceiver can be received by the computer (31) for analysis by the particle analysis application (150). For brevity, certain elements shown in FIG. 10 are not duplicated in FIG. 11 but it should be understood that the embodiment of the flow cytometer (24) shown in FIG. 11 with multiple nozzles includes and can otherwise function as described above.

Figure 12:
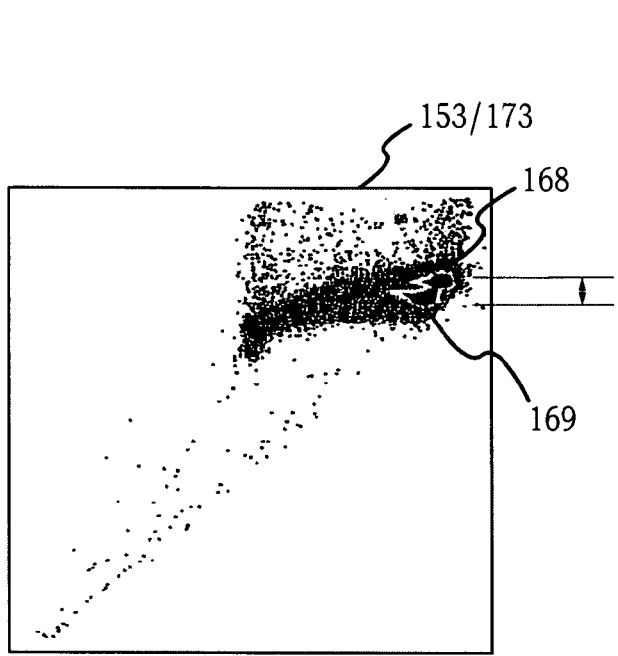
FIG. 12 is a histogram of sperm cells entrained in a fluid flow regulated in accordance with the invention differentiated into X-chromosome bearing and Y-chromosome bearing populations.
Figure 13:
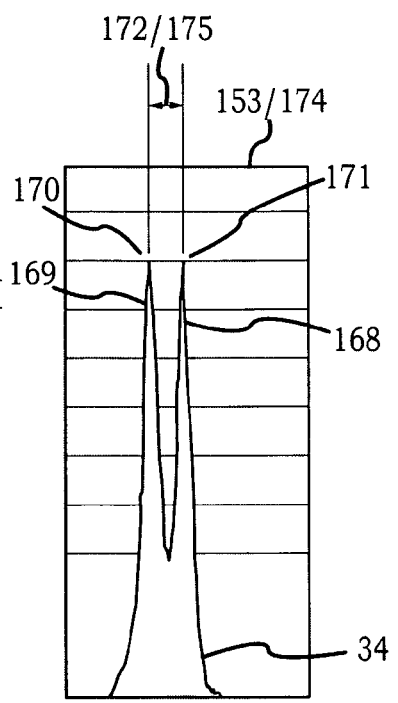
FIG. 13 is a bivariate plot of sperm cells entrained in a fluid flow regulated in accordance with the invention differentiated into X-chromosome bearing and Y-chromosome bearing populations.

FIGS. 12 and 13 show particular examples of viewable data representations (153) from the analysis of a plurality of sperm cells (133) using the fluid processing system including fluid flow characteristic regulator (58) above-described. Specifically, FIG. 12 is a bivariate plot (173) showing two prominent sub-populations of a plurality of sperms cells (163) analyzed and sorted by a flow cytometer, as above-described. The first sub-population including X-chromosome bearing sperm cells (168) and the second subpopulation including Y-chromosome bearing sperm cells (169). FIG. 13 provides a chromatogram (174) showing a first peak (170) representing first sub-population including X-chromosome bearing sperm cells (168) and a second peak (171) representing the second sub-population second subpopulation including Y-chromosome bearing sperm cells (169). The first peak (170) and the second peak (171) can have greater or lesser degree of resolution (175) as indicated by the distance (172) between the apex of the first peak (170) and the apex of the second peak (171). The operating parameters of the flow cytometer (24) can be adjusted as to sheath fluid flow rate, sample fluid flow rate, sheath fluid pressure, sample fluid pressure, event rates as described below, or the like to increase or decrease the resolution (175) to the extent possible or depending upon the application. An advantage of using the fluid processing system including the fluid flow characteristic regulator (58) above-described can be that the fluid flow (11) received by the flow cytometer (24) from the fluid flow outlet (63) can be less variable as to certain fluid flow characteristics (59) (as above described) which can result in a greater resolution (175) or greater consistency in resolution (175) over a period of time or make operation of the flow cytometer (24) more consistent as to formation of droplets (140) or droplet break-off point (141), or the like.

Example 1

Figure 14:
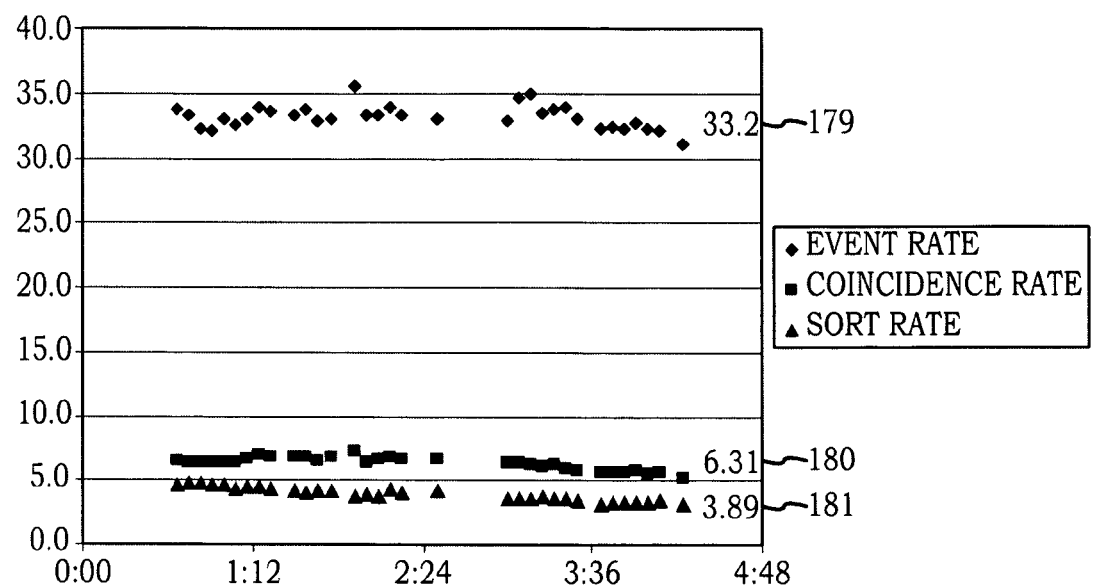
FIG. 14 is a graph which plots event rates, coincidence rates, and sort rates over the period of time in which sperm cells are sorted into X-chromosome bearing and Y-chromosome bearing populations using a FACS which receives a fluid flow regulated with a particular embodiment of a fluid flow characteristic regulator.

Now referring primarily to Table 1 and FIGS. 10 and 14, which provides an example of the performance of the inventive fluid processing system including the fluid flow characteristic regulator (58) with a MOFLO® SX flow cytometer (24) in analyzing a plurality of sperm cells (163) and isolate the X chromosome bearing sperm cells (168) (the Y-chromosome bearing sperm cells (169) were not collected). The plurality of sperm cells (163) were obtained as ejaculate from a Brahma bull (Bull No. BR736). The plurality of sperm cells (163) obtained from the Brahma bull were stained with Hoescht 33342 and sorted according to the method summarized in "Current Status of Sexing Mammalian Spematozoa", G. E. Seidel, et. al., Reproduction (2002), 124, 733-743. Compared to other bovids such as Holstein, Jersey, Angus, and the like, it can be more difficult to isolate the sperm cells (163) obtained from Brahma bulls into sub-populations of X-chromosome bearing sperms (168) and Y-chromosome bearing sperm cells (169) because the difference in the amount of light emitted (145) upon interrogation of DNA (164) stained sperm cells (163) can be less than for other breeds of bulls.

As a control, sperm cells (163) of Bull No. BR736 were analyzed and sorted in accordance with conventional procedures using the MOFLO® SX flow cytometer (24) without use of the inventive fluid processing system or the fluid flow characteristic regulator (58) to establish a sub-population of about 10 million X-chromosome bearing sperm cells (168).

The inventive fluid processing system including the fluid flow characteristic regulator (58) was then connected as above-described to the MOFLO® SX flow cytometer (24) and four sex selected of sperm cells (163) each containing about 10 million X-chromosome bearing sperm cells (168) were collected within the subsequent three and one-half hour period of time. The MOFLO® SX flow cytometer (24) was adjusted to sort about 35% to about 38% of the sperm cells (163) oriented so that either the front or back but not the side of the sperm cell (163) is interrogated by the light beam (142) (laser beam).

Now referring primarily to FIG. 14, which plots the actual event rates (number of sperm cells (163) interrogated by the light beam (142) per unit time) (179), the coincidence rates (more than one sperm cell is interrogated by the light beam (142) at the same time) (180), and sort rates (the number of X-chromosome bearing sperm cells (169) isolated per unit time) (181) (the average numbers set out to the right of each plot) over the period of time in which the sperm cells (163) were analyzed and sorted. The drop delay (182) (see FIG. 10) for the MOFLO® SX flow cytometer (24) (elapse time while the cell is traveling from the light beam (laser beam) interrogation point to when it is in the last attached droplet) was established at 23 0/16 at the beginning of the analysis period, and when the drop delay was checked at the end of the analysis period it had remained at substantially the same value.

Figure 15:
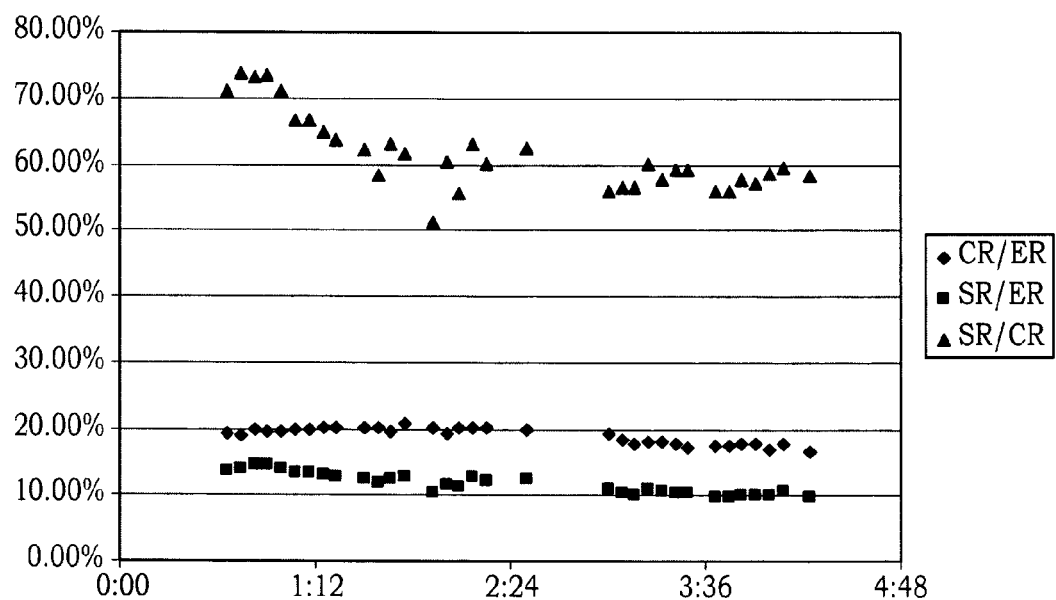
FIG. 15 is a graph which plots ratios of coincidence rate to event rate, sort rate to event rate, and sort rate to coincidence rate over the period of time in which sperm cells are sorted into X-chromosome bearing and Y-chromosome bearing populations using a FACS which receives a fluid flow regulated with a particular embodiment of a fluid flow characteristic regulator.

Now referring primarily to FIG. 15, which shows a plot of ratios of coincidence rate to event rate (183), sort rate to event rate (184), and sort rate to coincidence rate (185) over the duration of the about 3.5 hour analysis period. The event rate (179) is determined by the differential flow rates of the sheath fluid and the sample fluid. The co-incidence rate (180) is a subset of the event rate (179) typically comprising about 15-20% of the event rate (179). High co-incidence rates reduce the sort rate (181) and the resulting overall yield of cells sorted into respective sub-populations which can be collected. The overall yield of collected cells as a percentage of the original population of cells analyzed can be approximated by the ratio of the sort rate (181) divided by the event rate (179) ("SR/ER"). Coincidence as a percentage of the original plurality of particles, cells or sperm cells analyzed can be approximated by the ratio of coincidence rate (180) divided by the event rate (179) ("CR/ER"). The inefficiency in overall yield caused by high coincidence rate (180) can be reduced by lowering the event rate (179). Lowering the event rate (179) can lower the sort rate (181), reducing the economic value of the time sorted, as less cells are sorted in a specified time. Accordingly, the balance between highest possible event rate (179) to maximize sort rate (181) and an appropriately minimized event rate (179) to minimize coincidence rate (180) are best balanced by calculating the ratio of SR/CR ((sort rate (181) divided by the coincidence rate (180)). Further, in practice, this ratio should be kept as stable as possible to assure the optimum is achieved over time. The plot of the SR/CR ratio in FIG. 15 shows the 3.5 hour analysis period with ovals showing three time periods of this ratio. Each time period depicts the data derived from on uniquely stained sample. The first time period shows a slightly falling trend that is created by changes in the resolution of analysis and an operator adjustment to lower sort rate (181). The second period shows a volatile trend which is caused by the operator purposefully adjusting the distance (178) between a magnetic material (122) and a Hall Effect sensor (108) in the fluid flow characteristic regulator (58), such that the flexible barrier (68) becomes tensed, causing the pressure of sheath fluid to rise slightly, causing the event rate (179) fall slightly. Upon readjustment to a non-tensed position of the flexible barrier (68), the situation is reversed. The third period shows a very stable trend which is created by the operator keeping the flexible barrier (68) at a medium position, such that pressure remains stable without any variation caused by the flexible barrier (68) becoming tensed. The third period comprises two stained samples.

Each of the four samples were taken through conventional post-sort handling, using 2×7.5 ml of 12% TRIS Medium). After centrifuging and decanting, 1 ml of cold TRIS A/B extender was added. This brought the volume to about 1.4 ml. For each of the 5 samples, 5 straws were filled by hand, with about 0.225 ml of fluid remaining. The "calculated" concentration is therefore about 1.65 mio/ml. (Thom can you add in the details to this paragraph).

The purity, the motility and the progressive motility of each of the four isolated subpopulations of X-chromosome bearing sperm cells (168) was assessed and the data set out in Table 1.

TABLE 1

|  | Sperm Concentration | X-Purity (% X sperm) | Motility (%) | Progressive Motility (%) |
| --- | --- | --- | --- | --- |
| Control | 1.67 | 94.50% | 39.30% | 29.00% |
| Sample 1 | 1.46 | 92.50% | 37.40% | 25.00% |
| Sample 2 | 1.68 | 92.00% | | |
| Sample 3 | 1.60 | 93.50% | | |
| Sample 4 | 1.55 | 93.00% | | |

In summary, the data of Table 1 and FIGS. 14 and 15 indicate that the inventive fluid processing system including the fluid flow characteristic regulator (58) can be utilized with instruments such as flow cytometers (24), and other microfluid instruments such as high performance liquid chromatographs, to make more consistent fluid flow characteristics

(59) to achieve consistent fluid flow (11) in the fluid flow paths (61) of such instruments and achieve consistent results in the analysis of particles entrained in such fluid flow (11). Specifically, with respect to the analysis and flow sorting of a plurality of sperm cells (163), results can be achieved which are comparable to convention flow analysis and flow sort procedures even when the fluid flow (11) is generated by a fluid flow generator (10) (such as a dual piston high performance liquid chromatography pump) which introduces adverse fluid flow characteristics (59) (increased pulsation or pressure wave forms) in the fluid flow (11).

As can be easily understood from the foregoing, the basic concepts of the present invention may be embodied in a variety of ways. The invention involves numerous and varied embodiments of a fluid flow characteristic regulator (58) which can be utilized with microfluid instruments (176) such as high performance liquid chromatographs (12) or flow cytometers (24) to control variation in fluid flow characteristics (59).

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "fluid flow characteristic regulator" should be understood to encompass disclosure of the act of "regulating fluid flow characteristics"—whether explicitly discussed or not—and, conversely, were there effectively disclosure of the act of "regulating fluid flow characteristics", such a disclosure should be understood to encompass disclosure of a "fluid flow characteristic regulator" and even a "means for regulating fluid flow characteristics." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Webster's Unabridged Dictionary, each definition hereby incorporated by reference.

Thus, the applicant(s) should be understood to claim at least: i) each of the fluid flow characteristic regulators herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth below are intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A fluid flow characteristic regulator, comprising:
a) a fluid flow path;
b) a control fluid flow path adjacent said fluid flow path;
c) a flexible barrier located between said fluid flow path and said control fluid flow path, wherein the flexible barrier has a first barrier surface defining a portion of the fluid flow path and a second barrier surface defining a portion of the control flow path;
d) a fluid flow variation sensor positioned within the fluid flow characteristic regulator to sense movement of said flexible barrier in response to a fluid flow in said fluid flow path, wherein the fluid flow variation sensor generates a fluid flow variation signal based upon movement of the flexible barrier;
e) a fluid flow variation signal analyzer in communication with the fluid flow sensor, wherein the fluid flow variation signal analyzer generates control fluid adjustment values in response to said fluid flow variation signal;
f) a control fluid delivery adjustment element in communication with the fluid flow variation signal analyzer, wherein the control fluid delivery adjustment element converts said control fluid adjustment values to corresponding control fluid delivery adjustment values; and g) a control fluid controller in communication with the control fluid delivery adjustment element, wherein the control fluid controller adjusts control fluid characteristics of a control fluid in said control fluid path based on said control fluid deliver adjustment values.

2. The fluid flow characteristic regulator of claim 1, wherein said fluid flow in said fluid flow path comprises a liquid flow and wherein the liquid flow is selected from the group consisting of a liquefied gas, a solvent, an alcohol, an acid, a base, an organic solvent, a solution containing an amount of solute, a sheath fluid for a flow cytometer, a TRIS buffer, and a mobile phase for a chromatograph.

3. The fluid flow characteristic regulator of claim 1, wherein said control fluid comprises a control gas flow wherein the gas flow is selected from the group consisting of argon, nitrogen, carbon dioxide, helium, oxygen, a mixture of gases, and atmospheric gases.

4. The fluid flow characteristic regulator of claim 3, wherein said control fluid controller comprises a gas pressure controller of a flow cytometer.

5. The fluid flow characteristic regulator of claim 2, further comprising a fluid flow generator.

6. The fluid flow characteristic regulator of claim 5, wherein said fluid flow generator comprises a reciprocating piston pump.

7. The fluid flow characteristic regulator of claim 1, further comprising a first regulator portion having a configuration which engages a first barrier surface of said flexible barrier to define said fluid flow path within said fluid flow characteristic regulator.

8. The fluid flow characteristic regulator of claim 7, further comprising a second regulator portion having a configuration which engages a second barrier surface of said flexible barrier to define said control fluid flow path within said fluid flow characteristic regulator said first regulator portion and said second regulator portion engaged to dispose adjacent said fluid flow path and said control fluid flow path.

9. The fluid flow characteristic regulator of claim 8, wherein said a fluid flow variation sensor comprises a magnetic material disposed in opposed relation to a hall effect sensor and wherein said fluid flow variation signal comprises a variation in voltage of said hall effect sensor.

10. The fluid flow characteristic regulator of claim 9, wherein said fluid flow variation signal analyzer operates to correspondingly match said variation in voltage to a voltage variation value.

11. The fluid flow characteristic regulator of claim 1, wherein said fluid flow variation signal analyzer further operates to correspondingly match said voltage variation value to said control fluid adjust values.

12. The fluid flow characteristic regulator of claim 1, further comprising a fluid source containing an amount of sheath fluid fluidicly coupled to said fluid flow generator and wherein said fluid flow comprises a sheath fluid stream.

13. The fluid flow characteristic regulator of claim 12, further comprising a nozzle of a flow cytometer fluidicly coupled to said fluid flow path of said fluid flow characteristic regulator which receives said sheath fluid stream.

14. The fluid flow characteristic regulator of claim 13, wherein fluid flow comprises a plurality of sheath fluid streams each sheath fluid stream fluidicly coupled to a fluid flow characteristic regulator.

15. The fluid flow characteristic regulator of claim 14, further comprising a plurality of nozzles of a flow cytometer each fluidically coupled to said flow path of a corresponding fluid flow characteristic regulator.

16. The fluid flow characteristic regulator of claim 15, further comprising a particle source which entrains a plurality of particles in a sample fluid stream which joins said sheath fluid stream in said nozzle to exit said nozzle at a nozzle orifice as a coaxial laminar flow.

17. The fluid flow characteristic regulator of claim 16, further comprising a particle source which entrains a plurality of particles in a plurality of particle streams each of which correspondingly joins said sheath fluid stream in one of said plurality of nozzles of said flow cytometer.

18. The fluid flow characteristic regulator of claim 1, wherein said plurality of particles comprises one selected from the group consisting of: a plurality of cells; a plurality of sperm cells; and combinations thereof.

* * * * *